(12) United States Patent
Pijls

(10) Patent No.: US 7,775,988 B2
(45) Date of Patent: Aug. 17, 2010

(54) METHOD FOR DETERMINING THE BLOOD FLOW IN A CORONARY ARTERY

(75) Inventor: Nico H.J. Pijls, LG Valkenswaard (NL)

(73) Assignee: Radi Medical Systems AB, Uppsala (SE)

( * ) Notice: Subject to any disclaimer, the term of this patent is extended or adjusted under 35 U.S.C. 154(b) by 727 days.

(21) Appl. No.: 11/239,675

(22) Filed: Sep. 30, 2005

(65) Prior Publication Data

US 2007/0078352 A1    Apr. 5, 2007

(51) Int. Cl.
*A61B 5/02* (2006.01)
(52) U.S. Cl. ......................... 600/526; 600/504
(58) Field of Classification Search ................. 600/526
See application file for complete search history.

(56) References Cited

U.S. PATENT DOCUMENTS

| | | | |
|---|---|---|---|
| 3,446,073 A * | 5/1969 | Auphan et al. | 600/505 |
| 3,620,207 A * | 11/1971 | Sinclair | 600/505 |
| RE35,648 E | 11/1997 | Tenerz et al. | |
| 6,231,498 B1 * | 5/2001 | Pfeiffer et al. | 600/18 |
| 6,343,514 B1 | 2/2002 | Smith | |
| 6,471,656 B1 * | 10/2002 | Shalman et al. | 600/486 |
| 6,551,250 B2 * | 4/2003 | Khalil | 600/505 |
| 6,565,514 B2 | 5/2003 | Svanerudh et al. | |
| 6,754,608 B2 | 6/2004 | Svanerudh et al. | |
| 2003/0158490 A1 * | 8/2003 | Krivitski et al. | 600/504 |

OTHER PUBLICATIONS

Ganz et al.—"Measurement of Coronary Sinus Blood Flow by Continuous Thermodilution in Man", Circulation, vol. XLIV, Aug. 1971, pp. 181-195.
N.H.J. Pips et al.—"Coronary Pressure", $2^{nd}$ edition, Netherlands 2000.
Petra Johansson et al., "Blodflödesmätning i njurartären (Estimation of Renal Blood Flow)," Institutionen for Medicinsk Teknik KTH, Rapport 128, vol. 129, 2002, pp. 1-42.

* cited by examiner

*Primary Examiner*—Patricia C Mallari
(74) *Attorney, Agent, or Firm*—Foley & Lardner LLP

(57) ABSTRACT

The invention relates to a method and a system for determining the blood flow in an individual coronary artery of a patient, wherein the method comprises the steps of positioning a temperature sensor mounted at a distal portion of a guide wire at a distal position in the coronary artery, positioning an infusion catheter in the coronary artery such that the distal end of the infusion catheter is proximally of the temperature sensor, measuring the blood temperature with the temperature sensor, infusing cold indicator fluid with a known infusion rate and known or measurable temperature into the coronary artery by the infusion catheter, measuring the temperature of the mixture of blood and indicator fluid by the temperature sensor, and calculating the coronary blood flow by a formula based on the known and measured quantities. In an extended version, the method comprises steps for relating the calculated coronary flow value to related normal flow values, or related FFR values, or a related flow resistance.

15 Claims, 2 Drawing Sheets

METHOD FOR DETERMINING THE BLOOD FLOW IN A CORONARY ARTERY

FIELD OF THE INVENTION

The present invention relates generally to in vivo measurements of blood flow in vessels, and in particular to blood flow measurements in individual coronary arteries by means of a temperature sensitive sensor mounted on a guide wire and application of the thermodilution principle with continuous infusion of an indicator fluid.

BACKGROUND OF THE INVENTION

From the literature (e.g. Ganz et. al., "Measurement of coronary sinus blood flow by continuous thermodilution in man", Circulation 44:181-195, 1971) it is known that the thermodilution principle can be utilized for in vivo measurements of blood flow in the coronary sinus of human beings. These measurements involve the introduction of a specially designed catheter into the coronary sinus of a patient and injection of a cold indicator fluid from an injection orifice close to the catheter tip. The indicator fluid was flowing along the shaft of the catheter and caused a temperature drop in the blood temperature that was registered by several thermistors coupled in a Wheatstone-bridge arrangement. By knowledge of the indicator temperature and injection rate as well as the measured temperature drop caused by the injected indicator fluid, the coronary sinus flow can be estimated. This type of catheter, with its comparatively large outer diameter, can, however, not be used for measurements of blood flow in individual coronary arteries, and the method suffered also from a rather large variability within the measurements.

The U.S. Pat. No. 6,754,608, which is assigned to the present assignee, reveals that a temperature sensitive sensor mounted at a distal portion of a guide wire could be used for continuously monitoring of the temperature of blood passing the sensor. In use, a guide catheter is introduced to a proximal portion of an artery, and then the sensor guide wire is introduced into the guide catheter and is advanced until the sensor is located downstream of the catheter tip. When cold saline injected into the artery from the open catheter tip passes the temperature sensitive sensor, the sensor will register a temperature drop which is a function of blood flow. This patent is, however, directed to a system for measurements of coronary flow reserve (CFR), wherein a known amount of saline is injected as a bolus, and no suitable measures are taken to adapt the system to measurements of blood flow by continuous thermodilution. A special infusion catheter is, for example, not disclosed. It can further be noted that in the CFR procedure disclosed in U.S. Pat. No. 6,754,608, the temperature is not measured and presented as an absolute value, but instead the temperature drop triggers the start of a time measurement.

SUMMARY OF THE INVENTION

A first object of the present invention is therefore to provide a method for measuring coronary blood flow in individual coronary arteries by application of the thermodilution principle with continuous infusion of an indicator fluid. The invention also provides a system for carrying out the method.

For a specific patient and a specific medical situation it may be very valuable to obtain coronary blood flow as an absolute number, but it is also known that the coronary flow varies significantly between different individuals; and moreover the coronary flow of a patient who suffers from a coronary disease will change with the development of the disease, and the flow is also dependent on other individual and temporary medical circumstances. In other words, many times absolute values of coronary flow have a rather limited medical significance.

A second object of the present invention is therefore to provide a method for enhancing the medical usefulness of blood flow measurements, and in particular to provide a method with which absolute values of blood flow measured through application of the continuous thermodilution principle in a patient who suffers from a coronary disease can be related to normal blood flow values for this particular patient. The invention also provides a system for carrying out the method.

To achieve the object of providing a method for measuring coronary blood flow, the present invention provides a method comprising the following steps: positioning of a guide wire mounted temperature sensor at a distal position in a coronary artery of a patient, positioning of an infusion catheter in the coronary artery such that the distal end of the infusion catheter is located proximally (upstream) of the temperature sensor, measurement of blood temperature by the temperature sensor, continuous infusion of an indicator fluid (e.g. saline) with a known infusion rate and with known or measurable temperature through the infusion catheter, measurement of the temperature of the mixture of blood and indicator fluid by the temperature sensor, and calculation of absolute coronary flow according to a formula based on the known and measured quantities.

The above method comprises further preferably the induction of steady state hyperaemia in the patient, such that the obtained absolute coronary flow is the maximum absolute coronary flow. In a preferred embodiment of the invention, the temperature of the indicator fluid is measured by the same guide wire mounted temperature sensor as is used for measurements of blood and mixture temperatures. The positioning of the sensor guide wire and infusion catheter is usually accomplished through a guide catheter that has been inserted into the patient's aorta, and the method can be supplemented with a corresponding step.

To achieve the object of enhancing the medical usefulness of coronary blood flow measurements, the present invention also provides an extended version of the method, which comprises the following steps: positioning of a guide wire mounted temperature sensor at a distal position in a coronary artery of a patient, positioning of an infusion catheter in the coronary artery such that the distal end of the infusion catheter is located proximally (upstream) of the temperature sensor, induction of steady state hyperaemia in the patient, measurement of blood temperature by the temperature sensor, continuous infusion of an indicator fluid (e.g. saline) with a known infusion rate and with known or measurable temperature through the infusion catheter, measurement of the temperature of the mixture of blood and indicator fluid by the temperature sensor, calculation of maximum absolute coronary flow according to a formula based on the known and measured quantities, measurement of the hyperaemic aortic pressure, positioning of a guide wire mounted pressure sensor at a distal position in the coronary artery and measurement of a distal coronary pressure, calculation of a FFR (Fractional Flow Reserve) value as a ratio of the measured hyperaemic aortic pressure and the measured distal coronary pressure, and calculation of a related FFR value and/or calculation of a related normal maximal flow value according to formulas based on the known, measured and calculated quantities.

In preferred embodiments of the invention, the sensor guide wire as well as the infusion catheter is introduced into the coronary artery via a guide catheter inserted into the patient's aorta, and the hyperaemic aortic pressure is measured by a pressure transducer connected to the guide catheter. In another preferred embodiment, the distal coronary pressure and the blood temperature are measured with the same guide wire mounted sensor, i.e. the sensor is a temperature sensitive as well as pressure sensitive sensor. Optionally, the method can further include the following steps: positioning of a balloon arranged on a catheter in the coronary artery such that the balloon is positioned proximally (upstream) of the guide wire mounted pressure sensor, inflation of the balloon to create total occlusion of the coronary artery, and measurement of the coronary wedge pressure by the pressure sensor. The balloon is then deflated, and—like in the previous method—the temperature of the indicator fluid can preferably be measured by the same guide wire mounted temperature sensor as is used for measurements of blood and mixture temperatures. As will be discussed below, the method can, if needed, further be supplemented by a measurement of the venous pressure, which can be done through a multipurpose catheter placed in the right atrium of the patient's heart. Since all relevant perfusion pressures are measured and all relevant flows can be calculated, the method can further be supplemented with calculations of the myocardial, coronary and collateral resistances.

DETAILED DESCRIPTION OF THE PREFERRED EMBODIMENTS

Before describing the method according to the invention in detail, the theoretical framework on which the methods are based will be briefly presented. How the different parameters actually are obtained will be thoroughly explained below.

Figure 1:
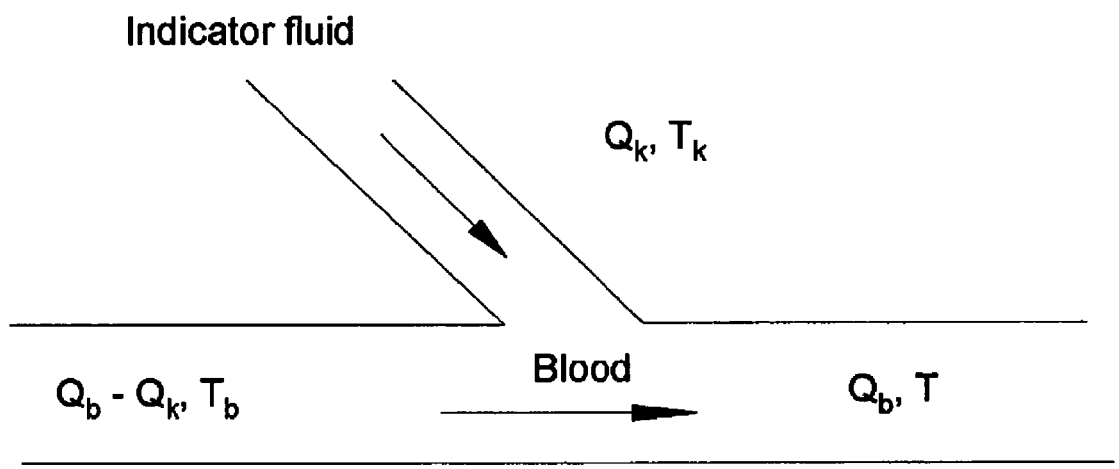
FIG. 1 illustrates a model that schematically illustrates the thermodilution principle with continuous infusion of indicator fluid.

With reference to FIG. 1, the absolute flow in a coronary artery of a patient, who is in a state of hyperaemia, can according to the present invention be calculated from the following equation $$Q_b = Q_k \frac{T_k - T_b}{T - T_b} \qquad \text{Eq. (1a)}$$

where $Q_b$ is the absolute coronary artery flow, $Q_k$ is the infusion rate of the indicator fluid, $T_k$ is the temperature of the indicator fluid, $T_b$ is the blood temperature, and $T$ is the temperature of the mixture of blood and indicator fluid. When the patient during the measurement is in hyperaemia, $Q_b$ will consequently be the maximum absolute coronary artery flow. The equation above is based on some assumptions and approximations, e.g. that the differences in density and specific heat of blood and indicator fluid, respectively, can be neglected, that complete mixing occurs between blood and indicator fluid, and that heat transfer to surrounding tissues is insignificant. It should also be noted that Eq. (1a) differs from the corresponding equation given in the above-referenced article by Ganz et. al. in that Eq. (1a) correctly presumes that injection of an indicator fluid leads to a decrease in the incoming blood flow in the coronary artery. When the infusion rate $Q_k$ of the indicator fluid is known and the temperature $T_k$ of the indicator fluid is known or measured, Eq. (1a) can, when the blood temperature $T_b$ before infusion of indicator fluid and the mixing temperature T after infusion of indicator fluid have been measured, be employed to calculate the absolute coronary flow $Q_b$. It can be noted that from a strict scientific point of view, it is not the infused fluid itself that is an indicator; rather it is the temperature (cold) of the infused fluid that is the indicator. However, as is customary within the field, the infused fluid (e.g. saline) will be referred to as the indicator fluid.

As mentioned above, Eq. (1a) is applicable in a situation where a patient is set in a state of hyperaemia such that the incoming blood flow can not be increased. If, on the other hand, the incoming blood flow can be increased, i.e. when the patient is not in hyperaemia, the following equation can be used $$Q_b = Q_k \frac{T - T_k}{T_b - T} \qquad \text{Eq. (1b)}$$

A calculation of maximum absolute coronary flow according to Eq. (1a) or Eq. (1b), where the included parameters have been obtained by temperature measurements in a patient who suffers from a coronary disease, will give the coronary flow at the patient's present state. For a specific patient and a specific medical situation it may be very valuable to obtain coronary blood flow as an absolute number, but many times such absolute numbers have a rather limited medical significance. Reasons for this are, for example, that for an individual patient the amount of myocardium to be perfused by a given coronary artery is not known and this amount of myocardium can also change over time. Further, a decreased blood flow can either mean a coronary stenosis or a microvascular disease, or a combination of both, i.e. a measured decrease in blood flow does not discriminate between these two factors. Furthermore, the coronary blood flow varies considerably between different individuals and arteries, and is also dependent on blood pressure. For a given patient suffering from a coronary disease, a measured value of maximum coronary blood flow can therefore not be compared with any "normal" value. If, for example, the patient suffers from a coronary stenosis, a measured flow value does not say much about the normal flow that would prevail if the patient were cured from this stenosis. Herein, the term "normal" is used to indicate the flow that would prevail in a healthy patient, e.g. when the patient is free from stenosis. It should in particular be noted that the term "normal"—unless otherwise explicitly stated— refers to the normal values for a specific patient, and not to, for example, some average values for a group of individuals. As was stated above, the present invention provides a method with which the measured flow in a patient suffering from a coronary disease can be related to normal flow values for this particular patient, i.e. the flow values that would prevail if the patient were cured from his or her disease. According to the invention this is accomplished through the concept of fractional flow reserve (FFR).

The concept of fractional flow reserve (FFR) is thoroughly explained in several medical articles. Herein special reference is made to the book "Coronary Pressure" by N. H. J. Pijls and B. De Bruyne, 2nd edition, Kluwer Academic Publishers, The Netherlands, 2000. Below only the most relevant relations will be presented; however, the entire contents of this book (including the description of various techniques and equipment) is incorporated herein by reference.

Figure 2:
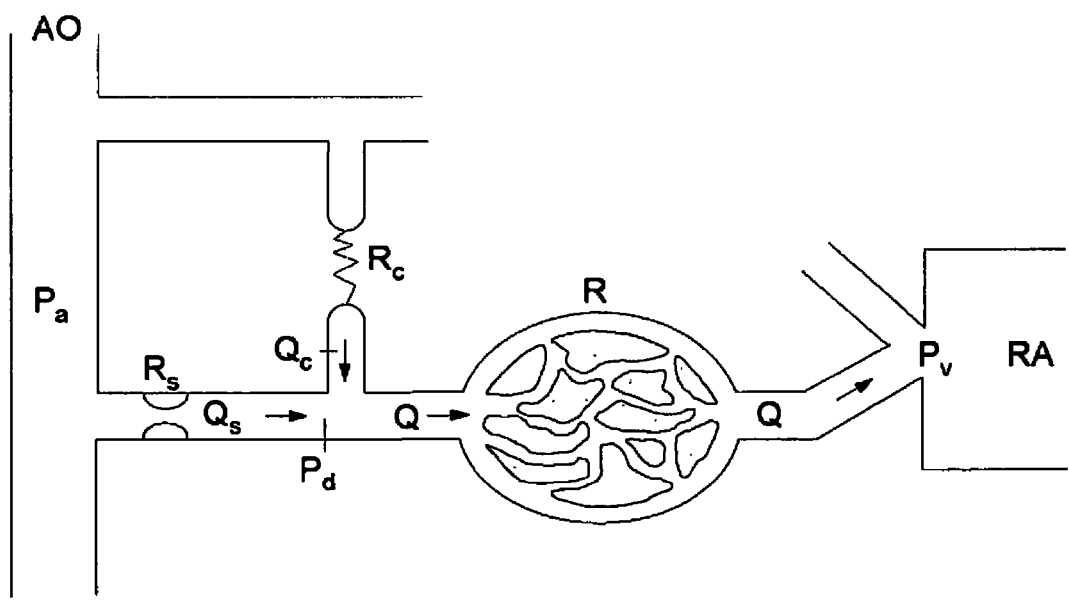
FIG. 2 illustrates schematically a model representing the coronary circulation.

The coronary circuitry is schematically illustrated in FIG. 2, where AO denotes the aorta and RA the right atrium, and $P_a$ represents arterial pressure in the aorta, $P_d$ distal coronary pressure, $P_v$ venous pressure, Q blood flow through the myocardial vascular bed, $Q_c$ collateral flow, $Q_s$ blood flow through the supplying epicardial coronary artery, R resistance of the myocardial vascular bed, $R_c$ resistance of the collateral circulation, and $R_s$ denotes the resistance of a stenosis in the supplying epicardial coronary artery. At total occlusion of the coronary artery, which can be artificially induced by inflating a balloon arranged at a catheter, the distal coronary pressure $P_d$ is called coronary wedge pressure and is denoted by $P_w$.

Now, the myocardial fractional flow reserve $FFR_{myo}$ is defined as the fraction of maximum flow that still can be maintained in spite of the presence of a stenosis, i.e. $FFR_{myo}$ indicates to what extent a patient is limited by his or her coronary artery disease, and consequently $FFR_{myo}$ is given by $$FFR_{myo} = \frac{\text{Maximum myocardial flow in the presence of a stenosis}}{\text{Normal maximum myocardial flow}} = \frac{Q}{Q^N} \quad \text{Eq. (2)}$$

where the superscript N indicates the normal value of the respective quantity, and therefore, by definition, $Q^N = Q_s^N$ and $Q_c^N = 0$. In analogy to myocardial fractional flow reserve, coronary fractional flow reserve $FFR_{cor}$ can be defined as maximum coronary artery blood flow in the presence of a stenosis divided by normal maximum coronary artery flow. Thus, $$FFR_{cor} = \frac{\text{Maximum coronary flow in the presence of a stenosis}}{\text{Normal maximum coronary flow}} = \frac{Q_s}{Q_s^N} \quad \text{Eq. (3)}$$

The ratio of collateral blood flow to normal maximum myocardial flow is consequently written as $Q_c/Q^N$ and is called fractional collateral flow; and the quantity $(Q_c/Q^N)_{max}$ is the maximum recruitable collateral flow as may be encountered during coronary artery occlusion.

All these quantities, $FFR_{myo}$, $FFR_{cor}$, $Q_c/Q^N$ and $(Q_c/Q^N)_{max}$, can be obtained by measuring the different pressures in the coronary circuitry, and are given by $$(Q_c/Q^N)_{max} = \frac{P_w - P_v}{P_a - P_v} = const. \quad \text{Eq. (4)}$$

$$FFR_{cor} = \frac{P_d - P_w}{P_a - P_w} \quad \text{Eq. (5)}$$

$$FFR_{myo} = \frac{P_d - P_v}{P_a - P_v} \quad \text{Eq. (6)}$$

$$(Q_c/Q^N) = FFR_{myo} - FFR_{cor} \quad \text{Eq. (7)}$$

Here, Eq. (4) states the fundamental observation that $(Q_c/Q^N)_{max}$ is constant under conditions of maximum vasodilation. By definition $P_w$ can only be measured at coronary occlusion, and Eq. (4) can therefore be used to calculate $P_w$ as it would be at other $P_a$ during non-occluded states, e.g. before and after a percutaneous transluminal coronary angioplasty (PTCA) procedure.

From the above, it should now be clear that when the maximum coronary flow $Q_s$ has been measured in a patient suffering from a stenosis, and when the relevant pressures, i.e. $P_d$, $P_w$ and $P_a$, have been obtained for this particular patient such that $FFR_{cor}$ can be calculated through Eq. (5), then Eq. (3) can be used to calculate the normal maximum coronary flow $Q_s^N$ that this patient would have if he or she were cured from the stenosis. It should further be clear that, with knowledge of also the venous pressure $P_v$ and application of Eqs. (6) and (2), the maximum myocardial flow Q in the presence of a stenosis can be calculated. The collateral flow $Q_c$ can simultaneously be calculated as $Q_c = Q - Q_s$, and the fractional collateral flow can be calculated from Eq. (7). In fact, the concept of FFR gives the relation between myocardial, coronary and collateral flow both before and after a medical operation (e.g. PTCA) that removes a stenosis. If one of these parameters is calculated quantitatively, all the others are known as well.

From FIG. 2 it follows further that when a flow, such as the coronary artery flow, has been measured together with the relevant perfusion pressures, the different resistances R, $R_s$ and $R_c$ can be calculated. The resistance $R_s$ of a stenotic artery can, for example, be calculated as $$R_s = \frac{P_a - P_d}{Q_s} \quad \text{Eq. (8)}$$

At total occlusion, i.e. $R_s = \infty$ and $Q_s = 0$ such that $Q = Q_c$ and $P_d = P_w$, the myocardial resistance R can be calculated according to $$R = \frac{P_w - P_v}{Q} \quad \text{Eq. (9)}$$

while the collateral resistance $R_c$ can be obtained from $$R_c = \frac{P_a - P_w}{Q} \quad \text{Eq. (10)}$$

Having established the theoretical basis for the present invention, the practical details of a medical procedure for measuring blood flow in an individual coronary by application of the thermodilution principle with continuous infusion of an indicator fluid are now to be described. As already has been mentioned, the temperature as well as the pressure measurements are performed with a guide wire mounted sensor. Although it is within the scope of the present invention that the pressure measurements are executed by a specially dedicated pressure sensitive sensor, whereas the temperature measurements are executed with a separate, specially dedicated temperature sensitive sensor, both the pressure measurements and the temperature measurements are preferably accomplished with the same guide wire mounted sensor. A suitable guide wire mounted sensor is, for example, manufactured and sold by the Swedish company Radi Medical Systems AB under the registered trademark PressureWire® Sensor, and is inter alia described in the U.S. Pat. No. 6,343,514 and Re 35,648, which are assigned to the present assignee. The sensor signals representing the measured pressures and temperatures are advantageously processed in a specially dedicated device for monitoring, calculating and displaying the measured variables. Such a device is sold under the registered trademark RadiAnalyzer® by Radi Medical Systems AB, and is described in the U.S. Pat. No. 6,565,514, which is assigned to the present assignee. The entire contents of both '514 patents and the '648 patent (including the description of various techniques and equipment) is incorporated herein by reference.

When access to the artery of a patient has been obtained, the method according to the present invention usually commences with the introduction of a guide catheter into the patient's aorta, as is well-known in the field. If needed, a conventional guide wire can be employed to facilitate the introduction of the guide catheter, as also is well-known in the field. A guide wire mounted sensor is subsequently introduced into the guide catheter, and is then advanced out of the end of the guide catheter and into a specific coronary artery until the temperature sensor is located at a distal position in the coronary artery. A specially designed infusion catheter is then threaded onto the sensor guide wire, and is advanced along the sensor guide wire until the end of the infusion catheter is outside the end of the guide catheter and is located proximally (upstream) of the temperature sensor in the specific coronary artery. As an alternative, a conventional guide wire could be used to locate the specific coronary artery of interest, and the infusion catheter can thereafter be threaded over this conventional guide wire, which in a separate subsequent step is replaced by the sensor guide wire. It is even conceivable, and within the scope of the present invention, to position the infusion catheter in an individual coronary artery without any guidance by a guide wire. Furthermore, although a guide catheter usually is used in coronary interventions, it is not an absolute necessity for practising the present invention, and the invention, as defined by the claims, comprises embodiments wherein a guide catheter has been dispensed with. In such a case, a guide wire, with or without a sensor mounted thereon, an infusion catheter, or a combination of both, is utilized to locate a specific coronary artery without the assistance of a guide catheter; or a guide catheter could be removed before the temperature measurements commence.

Practical experiments have shown that a special infusion catheter is usually needed to achieve adequate mixing of blood and indicator fluid. As will be described below, in a preferred embodiment of the invention, the temperature of the indicator fluid is measured at the outlet of the infusion catheter such that any loss of heat through the infusion catheter mantle has no affect on the measurements. If, however, the temperature of the indicator fluid is measured more proximally of the distal tip, the infusion catheter should be designed to reduce loss of heat through the catheter mantle to a minimum. To ensure complete, or at least sufficient, mixing of indicator fluid and blood, a 2-3 F infusion catheter can be used. The infusion catheter should have a sufficient number of side holes provided along a distal portion thereof, the length of which can be in the order of 1-3 cm. Suitable infusion catheters are, for example, obtainable from the medical technology companies Boston Scientific or OCCAM. It should further be noted that the present method promotes complete mixing of blood and indicator fluid in that the indicator fluid flows away from the infusion catheter, rather than along the infusion catheter—as in the previously suggested method by Ganz et. al.

Figure 3:
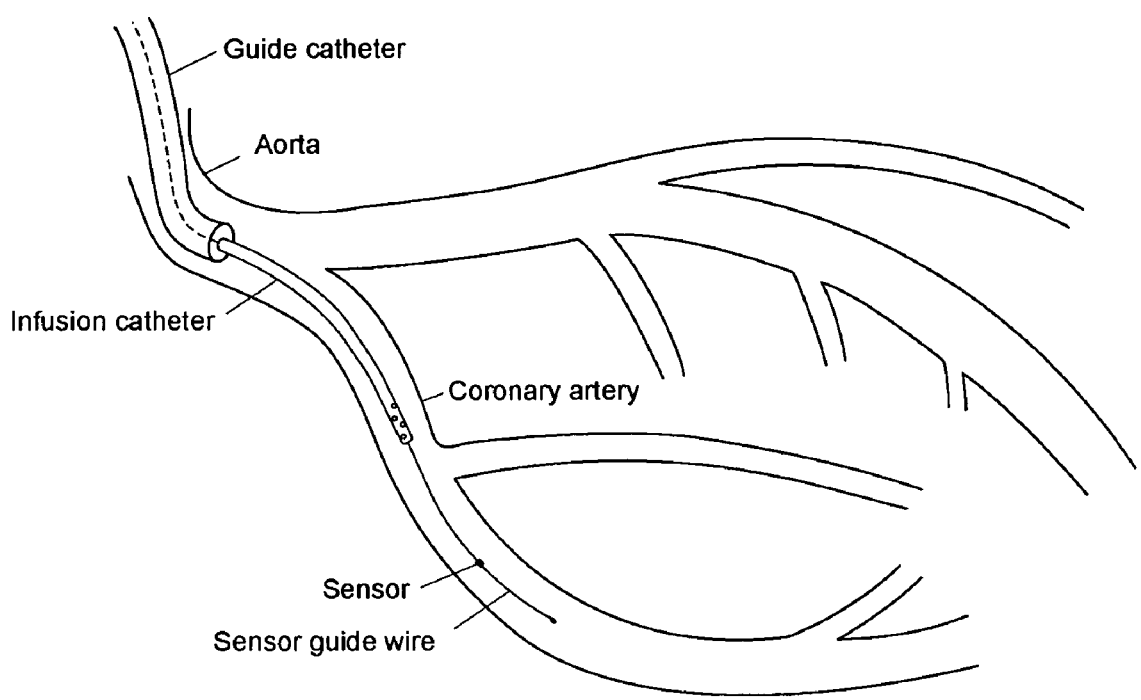
FIG. 3 is a schematic illustration of a coronary artery in which a guide catheter, an infusion catheter, and a guide wire mounted sensor have been positioned in order to perform the steps included in the method according to the present invention.

With a guide wire, a distal portion of which is provided with a temperature sensitive sensor, in place in a specific coronary artery, an infusion catheter is positioned over the sensor guide wire, and is advanced to a position proximally of the temperature sensor. As an alternative, the infusion catheter could first be positioned in a coronary artery (presumably by assistance of a conventional guide wire), and the sensor guide wire is then introduced into the infusion catheter, and is advanced out of the end of the infusion catheter to a distal position in the artery. The distance between the sensor and the infusion catheter end ranges from about 1 cm to 15 cm, preferably 3-6 cm, the important consideration being that complete mixing takes place between blood and indicator fluid. From the above it should be understood that the order of the first positioning steps is not crucial for practising the method; and the invention, as defined in the claims, encompasses all ways of inserting and positioning an infusion catheter and a sensor guide wire in a coronary artery. If a guide catheter is used, also this can be positioned in any suitable way without departing from the scope of the present invention. FIG. 3 illustrates schematically the respective locations of a guide catheter, an infusion catheter and a guide wire mounted sensor in a coronary artery.

With an infusion catheter and a temperature sensor correctly positioned in a coronary artery, the next step in the present method is to measure the blood temperature. This is accomplished by the temperature sensitive sensor arranged at the distal portion of the sensor guide wire. An example of a suitable sensor comprises a support body provided with a diaphragm covering a cavity formed in the support body. A pressure sensitive element is mounted on the diaphragm and a temperature sensitive resistor (or other component) with known temperature dependence is mounted in the vicinity of the pressure sensitive element. With this arrangement, which is disclosed in the above-mentioned U.S. Pat. No. 6,343,514, the output signal from the sensor is dependent on the temperature of the medium (i.e. blood) surrounding the sensor, and from the known temperature dependence the output signals can be converted to the temperature of the surrounding medium. The latter can, for example, be done in the device disclosed in the above-referenced U.S. Pat. No. 6,565,514. The output signals from this particular sensor are also dependent on the ambient pressure, and the sensor can thereby preferably be used to also measure the relevant blood pressures. It is, however, within the scope of the present invention to use other types of guide wire mounted sensors, as long as the outer diameter of the sensor guide is small enough to allow introduction into individual coronary arteries such that selective coronary artery flow can be measured.

When the blood temperature has been measured, cold indicator fluid, e.g. saline with a temperature well below the blood temperature, is injected into the infusion catheter and is further infused into the coronary artery. The indicator fluid mixes with the blood and causes a temperature drop, which is registered by the sensor. The indicator fluid is preferably stored in a thermally isolated reservoir, and is therefrom by a suitable device, such as a pump, delivered at a constant and known infusion rate. Clearly, the magnitude of the decrease in temperature at the measurement site will be a function of blood flow and temperature of indicator fluid; and with knowledge of these parameters, the absolute coronary flow in this particular artery can be calculated by application of Eqs. (1a) or (1b) above.

The temperature of the indicator fluid is preferably measured at the exit of the infusion catheter by the same guide wire mounted sensor as is used for the blood temperature measurements. This is accomplished by simply retracting the sensor guide wire until the sensor is located inside the infusion catheter and close to the distal exit opening of the infusion catheter. Advantageously, the temperature of the mixture of blood and indicator fluid is recorded during the retraction of the sensor guide wire, to thereby detect any inconsistencies or irregularities in the mixture temperature, which could arise due to incomplete mixing or other undesired flow phenomena. As an alternative, the temperature of the indicator fluid could be measured with some other device, such as a thermometer, e.g. at a position more proximally of the infusion catheter tip. The measurement of the indicator temperature could alternatively be performed before the mixing temperature is measured. It is also possible to perform the measurement of the blood temperature after the measurements of indicator and mixing temperatures.

The previously described method steps have provided the parameters necessary for calculating the blood flow prevailing in the coronary artery where the infusion catheter and sensor have been located, and, more specifically, for calculating the blood flow at the injection point of the indicator fluid. The measured parameters, i.e. the blood temperature $T_b$, the indicator fluid temperature $T_k$ and the mixture temperature T, together with the known infusion rate $Q_k$, can now be inserted into Eqs. (1a) or (1b) to thereby calculate the absolute coronary blood flow $Q_b$. Although it is not an indispensable prerequisite for the application of the thermodilution principle, a patient will normally be brought in a state of hyperaemia before the measurements take place. The flow calculated through Eq. (1a) will then be the maximum absolute coronary flow.

If the steps of the above method are conducted in a patient suffering from a flow restricting disease, such as a stenosis, the measured coronary flow will apparently be the momentary flow, which consequently depends on the present state of the stenosis. To be able to relate the measured flow to a normal flow for this particular patient, and to thereby enhance the medical usefulness of the flow measurement, the above method can be supplemented with further measurements using FFR. It is further possible to relate the measured maximum coronary flow to other flows, such as maximum myocardial flow or maximum collateral flow, or to different resistances prevailing in the coronary circuitry.

A measured blood flow in a stenotic artery is related to a normal, unstenotic flow value through the concept of fractional flow reserve (FFR), as is shown in Eqs. (2) and (3) above with reference to FIG. 2. For example, by dividing the maximum coronary flow $Q_s$ measured according to the method described above with the coronary fractional flow reserve $FFR_{cor}$, the normal (unstenotic) maximum coronary flow $Q_s^N$ is obtained for this particular coronary artery. Further, if the maximum myocardial flow Q in the presence of a stenosis is wanted, the measured coronary flow $Q_s$ is multiplied with $FFR_{myo}/FFR_{cor}$. In fact, it follows from Eqs. (2) to (7) that if one flow value is known, all the other flows, i.e. myocardial, coronary and collateral flows, can be calculated both with as well as without the presence of a stenosis.

A closer examination of Eqs. (4), (5) and (6) reveals that $FFR_{cor}$, $FFR_{myo}$ and $(Q_c/Q^N)_{max}$ can be obtained by measuring the relevant perfusion pressures. If, for example, the pressure $P_d$ distally of a stenosis, the aortic pressure $P_a$ proximally of the stenosis and the venous pressure $P_v$ all are measured, then the myocardial fractional flow reserve $FFR_{myo}$ can be calculated according to Eq. (6); and if total occlusion is created in the artery such that $P_v$ becomes the wedge pressure $P_w$, then $FFR_{cor}$ can be calculated from Eq. (5), while $(Q_c/Q^N)_{max}$ can be calculated from Eq. (4).

According to embodiments of the invention, the distal pressure $P_d$ (and, at total occlusion, the wedge pressure $P_w$) is measured with a guide wire mounted pressure sensor. In a preferred embodiment of the invention, this pressure sensor is the same sensor that is used for the previously described temperature measurements. Thus, the sensor is a temperature sensitive as well as pressure sensitive sensor. It is, however, also conceivable to use other types of guide wire mounted sensors, e.g. a temperature sensitive sensor could be used for the temperature measurements, while another, pressure sensitive sensor is used for the pressure measurements. The aortic pressure $P_a$ could be measured with a guide wire mounted sensor, e.g. the same sensor that is used for pressure measurements in a specific coronary artery, but a perhaps more common procedure would be to measure the aortic pressure $P_a$ with a pressure transducer connected to a guide catheter located in a patient's aorta, at the location of the ostium of the coronary artery. The latter is standard procedure during a vascular intervention. The venous pressure $P_v$ is known to be very low, on the order of a few mm/Hg. In many, or even most, cases the venous pressure $P_v$ can be neglected, i.e. be set to zero in the equations above. To actually measure the venous pressure is, however, a relatively simple procedure which is accomplished through the insertion of a multipurpose catheter in the right atrium of the patient's heart.

The wedge pressure $P_w$ deserves some attention. By definition, the wedge pressure $P_w$ is the pressure distally of a stenosis when the stenosis totally occludes the artery. As can be seen in FIG. 2, the myocardium is then perfused only through the collaterals. To measure the wedge pressure requires therefore that total occlusion is produced in the coronary artery. This can quite easily be artificially accomplished through the inflation of a balloon attached to a balloon catheter, which is introduced via a guide catheter. In a normal, healthy coronary artery, the coronary artery is, however, by itself capable of supplying the myocardium with enough blood, and no collaterals are developed. It should therefore be clear that for a normal artery, the distal coronary pressure $P_d$ is close to the aortic pressure $P_a$, and it follows consequently from Eqs. (5) and (6) that for an insignificant stenosis the coronary fractional flow reserve $FFR_{cor}$ is equal, or almost equal, to the myocardial fractional flow reserve $FFR_{myo}$; and $FFR_{myo}$ can therefore be substituted for $FFR_{cor}$ in Eq. (3) to calculate the normal maximum coronary flow $Q_s^N$, which is equal to the normal maximum myocardial flow $Q^N$. In short, for an insignificant stenosis, the extra step of creating total occlusion in an artery can often be omitted. On the other hand, for a severe stenosis, a medical intervention such as a PTCA must usually be undertaken, and such operation involves the creation of total occlusion and the wedge pressure can then simultaneously be measured without any extra efforts. When the relevant perfusion pressures have been measured and the relevant flows have been measured or calculated, different flow resistances can further be calculated through application of Eqs. (8), (9) and (10).

The method according to the present invention can now be summarized. The method comprises at least the steps of: (1) positioning a temperature sensor mounted at a distal portion of a guide wire or other member at a distal position in a coronary artery of a patient, (2) positioning an infusion catheter in the coronary artery such that the distal end of the infusion catheter is located proximally (upstream) of the temperature sensor, (3) measuring the blood temperature by the temperature sensor, (4) infusing a cold indicator fluid with a known infusion rate and known or measurable temperature into the coronary artery by the infusion catheter, (5) measuring the temperature of the mixture of blood and indicator fluid by the temperature sensor, and (6) calculating the coronary blood flow by an equation based on the known and measured quantities.

Preferably, the method comprises also the step of measuring the temperature of the indicator fluid, which is conveniently and advantageously done by retracting the sensor guide wire into the infusion catheter until the temperature sensor is located inside the infusion catheter and in the vicinity of the outlet opening of the infusion catheter. Usually the method also comprises the step of inducting steady state hyperaemia in the patient before the temperature measurements are done, such that the calculated blood flow is the maximum coronary blood flow, which is the clinically most relevant type of coronary blood flow. In practice, the method will often start with the introduction of a guide catheter into the aorta of the patient, and the infusion catheter and the sensor guide is then introduced via this guide catheter.

When the calculated coronary blood flow is to be related to other flows, such as myocardial or collateral flows, or is to be related to normal flow values for this particular patient, or when different flow resistances are to be calculated, the above method can be supplemented with further steps. The extended version of the method according to embodiments of the invention comprises at least the steps of: (1) positioning a temperature embodiments of sensor mounted at a distal portion of a guide wire at a distal position in a coronary artery of a patient, (2) positioning an infusion catheter in the coronary artery such that the distal end of the infusion catheter is located proximally (upstream) of the temperature sensor, (3) inducing steady state hyperaemia in the patient, (4) measuring the blood temperature by the temperature sensor, (5) infusing a cold indicator fluid with a known infusion rate and a known or measurable temperature into the coronary artery by the infusion catheter, (6) measuring the temperature of the mixture of blood and indicator fluid by the temperature sensor, (7) calculating the maximum coronary blood flow by an equation based on the known and measured quantities, (8) positioning a pressure sensor mounted at a distal portion of a guide wire at a distal position in the coronary artery, (9) measuring a distal pressure by the pressure sensor, (10) measuring the aortic pressure, (11) calculating a first fractional flow reserve (FFR) value based on the measured aortic and distal pressures, and (12) calculating a related flow value, or a related FFR value, based on the calculated maximum coronary flow and the first FFR value, or a related flow resistance based on the measured pressures and a calculated flow value.

Like before, the temperature of the indicator fluid is preferably measured with the temperature sensitive sensor, and in a preferred embodiment this sensor is also used for the pressure measurements, i.e. the sensor is a temperature sensitive as well as pressure sensitive sensor. It is, however, within the scope of the invention to use one guide wire mounted sensor for the pressure measurements and another guide wire mounted sensor for the temperature measurements. The aortic pressure can be measured with the guide wire mounted pressure sensor, but is most conveniently measured with a separate pressure transducer in fluid communication with a guide catheter which has been inserted into the patient's aorta, as is customary in cardiology practice. The method above can further be supplemented with a separate measurement of the venous pressure, which can be accomplished by a multipurpose catheter, which is introduced into the right atrium of the patient's heart and which is in fluid communication with a pressure transducer. In many cases, the venous pressure can, however, be neglected, i.e. set to zero, in the different calculations. The calculation of some FFR values requires knowledge of the so-called wedge pressure, which, by definition, can only be obtained at total occlusion of the coronary artery. Total occlusion can be artificially induced by inflating a balloon provided at a balloon catheter introduced into the coronary artery, for example via the above-mentioned guide catheter. The method above can therefore be supplemented with the steps of inducing total occlusion and measuring the wedge pressure. In many cases, e.g. for an insignificant stenosis, the distal coronary pressure is equal, or almost equal, to the aortic pressure, and the wedge pressure can be neglected in the different calculations.

Besides the method described above, preferred embodiments of the present invention also provide a system for carrying out the method. Such a system comprises an infusion catheter adapted to be introduced into a coronary artery, a guide wire having a distal portion provided with a temperature sensitive sensor and being adapted for insertion into a coronary artery, a device for transforming the output signals from the temperature sensor into a temperature of the medium surrounding the sensor, and a device which is adapted to be connected to the infusion catheter for continuously delivering a cold indicator fluid into the coronary artery. The system can further be supplemented with a guide catheter adapted to be introduced into the aorta of a patient.

When the system is utilized for carrying out the extended version of the method, in which FFR values are to be obtained, the system comprises further a pressure sensitive sensor mounted at a distal portion of a guide wire. This pressure sensor is in a preferred embodiment, the same sensor as is used for the temperature measurements. The system can further be supplemented with a pressure transducer adapted to be connected to the guide catheter for measuring the aortic pressure. In another embodiment, the system also comprises a multipurpose catheter adapted to be inserted into the right atrium of a patient and adapted to be connected to a pressure transducer for measurement of the venous pressure.

Although the present invention has been described with reference to specific embodiments, also shown in the appended drawings, it will be apparent for those skilled in the art that many variations and modifications can be done within the scope of the invention as described in the specification and defined with reference to the claims below. It should in particular be noted that the skilled person would recognize that the relative order of some of the steps in the method can be changed without affecting the outcome of the method. Also, different ways of positioning the different instruments, e.g. the sensor guide wire and the infusion and guide catheters, at their respective positions can be employed without departing from the scope of the invention. As discussed above, blood temperature is preferably measured with the same temperature sensor that is used for measurement of the mixture temperature, but it is conceivable to use a separate sensor for the blood temperature measurement, especially if this extra sensor and the guide wire mounted temperature sensor are calibrated to each other. A separate temperature sensor would, for example, allow continuous measurement of the blood temperature during the whole thermodilution procedure.

What is claimed is:

1. A method for determining a blood flow in an individual coronary artery of a patient, comprising at least the following steps:

positioning a temperature sensor mounted at a distal portion of a guide wire at a distal position in the coronary artery;

positioning an infusion catheter in the coronary artery such that a distal end of the infusion catheter is proximally of the temperature sensor;

measuring blood temperature;

infusing cold indicator fluid with a known infusion rate and known or measurable temperature into the coronary artery using the infusion catheter;

measuring a temperature of a mixture of blood and indicator fluid using the temperature sensor, wherein measuring the temperature of the mixture of blood and indicator fluid using the temperature sensor comprises retracting the temperature sensor towards the distal end of the infusion catheter while measuring the temperature of the mixture of blood and indicator fluid; and calculating the coronary blood flow by a formula including at least the measured blood temperature, the known infusion rate, the known or measurable cold indicator fluid temperature, and the measured mixture temperature.

2. A method for determining a blood flow in an individual coronary artery of a patient, comprising at least the following steps:

positioning a temperature sensor mounted at a distal portion of a guide wire at a distal position in the coronary artery;

positioning an infusion catheter in the coronary artery such that a distal end of the infusion catheter is proximally of the temperature sensor;

measuring blood temperature;

infusing cold indicator fluid with a known infusion rate and known or measurable temperature into the coronary artery using the infusion catheter;

measuring a temperature of a mixture of blood and indicator fluid using the temperature sensor; and calculating the coronary blood flow by a formula including at least the measured blood temperature, the known infusion rate, the known or measurable cold indicator fluid temperature, and the measured mixture temperature;

further comprising the step of retracting the temperature sensor until the temperature sensor is located inside the infusion catheter and measuring the indicator fluid temperature at the end of the infusion catheter.

3. A method for determining a blood flow in an individual coronary artery of a patient, comprising at least the following steps:

positioning a temperature sensor mounted at a distal portion of a guide wire at a distal position in the coronary artery;

positioning an infusion catheter in the coronary artery such that a distal end of the infusion catheter is proximally of the temperature sensor;

measuring blood temperature;

infusing cold indicator fluid with a known infusion rate and known or measurable temperature into the coronary artery using the infusion catheter;

measuring a temperature of a mixture of blood and indicator fluid using the temperature sensor, wherein measuring the temperature of the mixture of blood and indicator fluid using the temperature sensor comprises varying distance between the temperature sensor and the distal end of the infusion catheter; and calculating the coronary blood flow by a formula including at least the measured blood temperature, the known infusion rate, the known or measurable cold indicator fluid temperature, and the measured mixture temperature;

further comprising the step of inducing steady state hyperaemia in the patient before temperature measurement such that the calculated coronary blood flow is a maximum coronary blood flow.

4. A method for determining a blood flow in an individual coronary artery of a patient, comprising at least the following steps:

positioning a temperature sensor mounted at a distal portion of a guide wire at a distal position in the coronary artery;

positioning an infusion catheter in the coronary artery such that a distal end of the infusion catheter is proximally of the temperature sensor;

measuring blood temperature;

infusing cold indicator fluid with a known infusion rate and known or measurable temperature into the coronary artery using the infusion catheter;

measuring a temperature of a mixture of blood and indicator fluid using the temperature sensor;

calculating the coronary blood flow by a formula including at least the measured blood temperature, the known infusion rate, the known or measurable cold indicator fluid temperature, and the measured mixture temperature; and inducing steady state hyperaemia in the patient before temperature measurement such that the calculated coronary blood flow is a maximum coronary blood flow, wherein the formula used for calculating the coronary blood flow is:

$$Q_b = Q_k \frac{T_k - T_b}{T - T_b}$$

where $Q_b$ is the coronary blood flow, $Q_k$ is the known infusion rate of the indicator fluid, $T_k$ is the known or measurable temperature of the indicator fluid, $T_b$ is the measured blood temperature, and $T$ is the measured temperature of the mixture of blood and indicator fluid.

5. The method according to claim 1, wherein the formula used for calculating the coronary blood flow is:

$$Q_b = Q_k \frac{T - T_k}{T_b - T}$$

where $Q_b$ is the coronary blood flow, $Q_k$ is the known infusion rate of the indicator fluid, $T_k$ is the known or measurable temperature of the indicator fluid, $T_b$ is the measured blood temperature, and $T$ is the measured temperature of the mixture of blood and indicator fluid.

6. A method for determining a blood flow in an individual coronary artery of a patient and for relating this blood flow to at least one related flow value or to at least one related fractional flow reserve (FFR) value, comprising at least the following steps:

positioning a temperature sensor mounted at a distal portion of a guide wire at a distal position in the coronary artery;

positioning an infusion catheter in the coronary artery such that a distal end of the infusion catheter is proximally of the temperature sensor;

inducing steady state hyperaemia in the patient;

measuring a blood temperature with the temperature sensor;

infusing cold indicator fluid with a known infusion rate and known or measurable temperature into the coronary artery using the infusion catheter;

measuring a temperature of a mixture of blood and indicator fluid using the temperature sensor;

calculating a maximum coronary blood flow by a formula including at least the measured blood temperature, the known infusion rate, the known or measurable cold indicator fluid temperature, and the measured mixture temperature;

positioning a pressure sensor mounted at a distal portion of the guide wire at a distal position in the coronary artery;

measuring a distal pressure by the pressure sensor;

measuring the aortic pressure;

calculating a first FFR value based on the measured aortic and distal pressures; and calculating a related flow value, or a related FFR value, based on the calculated maximum coronary blood flow and the first FFR value, or a related flow resistance based on the measured aortic and distal pressures and the calculated maximum coronary blood flow.

7. The method according to claim 6, further comprising the step of retracting the temperature sensor until the temperature sensor is located inside the infusion catheter and measuring the indicator fluid temperature at the end of the infusion catheter.

8. The method according to claim 6, wherein the temperature measurements and the measurement of the distal pressure are executed with the same guide wire mounted sensor.

9. The method according to claim 6, wherein the temperature measurements, the measurement of the distal pressure, and the measurement of the aortic pressure are executed with the same guide wire mounted sensor.

10. The method according to claim 6, wherein the measurement of the aortic pressure is executed with a pressure transducer connected to a guide catheter inserted into the patient's aorta.

11. The method according to claim 6, further comprising the step of inserting a catheter into a right atrium of the patient's heart and measuring venous pressure by a pressure transducer connected to the catheter.

12. The method according to claim 6, further comprising the step of positioning a balloon arranged at a catheter to a position proximally of the pressure sensor, inflating the balloon to completely occlude the coronary artery, and measuring coronary wedge pressure using the pressure sensor.

13. The method according to claim 1, further comprising the step of measuring the blood temperature with the temperature sensor.

14. The method according to claim 1, wherein the infusing comprises continuous infusing.

15. The method according to claim 1, wherein the method uses only one temperature sensor.

* * * * *